(12) United States Patent
Nelvig et al.

(10) Patent No.: US 8,317,996 B2
(45) Date of Patent: Nov. 27, 2012

(54) AUXILIARY DEVICE, A MARINE SURFACE VESSEL AND A METHOD FOR A SACRIFICIAL ANODE IN A MARINE CONSTRUCTION

(75) Inventors: Carl Nelvig, Göteborg (SE); Petter Igede, Göteborg (SE)

(73) Assignee: AB Volvo Penta, Göteborg (SE)

( * ) Notice: Subject to any disclaimer, the term of this patent is extended or adjusted under 35 U.S.C. 154(b) by 158 days.

(21) Appl. No.: 12/997,639

(22) PCT Filed: Jun. 25, 2008

(86) PCT No.: PCT/SE2008/000409
§ 371 (c)(1),
(2), (4) Date: Dec. 13, 2010

(87) PCT Pub. No.: WO2009/157815
PCT Pub. Date: Dec. 30, 2009

(65) Prior Publication Data
US 2011/0089048 A1    Apr. 21, 2011

(51) Int. Cl.
*C23F 13/04*    (2006.01)
*C23F 13/20*    (2006.01)
*C23F 13/22*    (2006.01)

(52) U.S. Cl. ........ 205/740; 205/725; 205/727; 205/730; 204/196.02; 204/196.04; 204/196.06; 204/196.07; 204/196.1; 204/196.11; 204/196.21; 204/196.26; 204/196.36; 324/425; 324/71.2

(58) Field of Classification Search ............. 205/740, 205/725, 727, 730; 204/196.02, 196.04, 204/196.06, 196.07, 196.1, 196.11, 196.21, 204/196.26, 196.36; 324/425, 71.2
See application file for complete search history.

(56) References Cited

U.S. PATENT DOCUMENTS 3,410,771 A     11/1968  Sudrabin et al.
5,627,414 A  *  5/1997   Brown et al. ............ 205/726
(Continued)

OTHER PUBLICATIONS

International Search Report for corresponding International App. PCT/SE2008/000409.

*Primary Examiner* — Bruce Bell
(74) *Attorney, Agent, or Firm* — WRB-IP LLP (57) ABSTRACT

A method is provided for corrosion protection in a marine construction, such as a marine surface vessel or a marine structure, the marine construction including at least one metal element and a sacrificial anode adapted to be at least partly immerged in an electrolyte in the form of water, in which the marine construction is at least partly immerged, the at least one metal element including a metal part, the sacrificial anode being provided for corrosion protection of the metal part. The method includes connecting at least one of the at least one metal element and the sacrificial anode to a DC electrical power outlet so as to allow an electric de-passivation current through an electrical circuit including the sacrificial anode, the metal element and the electrolyte.

13 Claims, 5 Drawing Sheets

U.S. PATENT DOCUMENTS

| | | | | |
|---|---|---|---|---|
| 5,999,107 A * | 12/1999 | Cooper et al. | ............ | 340/870.16 |
| 6,183,625 B1 * | 2/2001 | Staerzl | ............ | 205/727 |
| 7,044,075 B2 | 5/2006 | Sica | | |
| 7,238,263 B2 * | 7/2007 | Howard et al. | ............ | 204/196.03 |
| 7,381,312 B1 * | 6/2008 | Misorski et al. | ............ | 204/196.18 |
| 8,118,983 B1 * | 2/2012 | Anderson et al. | ............ | 204/196.11 |
| 8,226,812 B2 * | 7/2012 | Nelvig et al. | ............ | 205/740 |
| 2006/0054072 A1 * | 3/2006 | Sica et al. | ............ | 114/222 |
| 2006/0065551 A1 * | 3/2006 | Howard et al. | ............ | 205/740 |
| 2006/0070871 A1 * | 4/2006 | Bushman et al. | ............ | 204/196.01 |
| 2006/0163084 A1 * | 7/2006 | Chang et al. | ............ | 205/724 |
| 2011/0000794 A1 * | 1/2011 | Nelvig et al. | ............ | 205/726 |
| 2011/0083973 A1 * | 4/2011 | Nelvig | ............ | 205/724 |
| 2011/0290665 A1 * | 12/2011 | Shim | ............ | 205/726 |

* cited by examiner

AUXILIARY DEVICE, A MARINE SURFACE VESSEL AND A METHOD FOR A SACRIFICIAL ANODE IN A MARINE CONSTRUCTION

The present invention relates to an auxiliary device, a marine surface vessel, and to a method for corrosion protection in a marine construction, such as a marine surface vessel or a marine structure, the marine construction comprising at least one metal element and a sacrificial anode adapted to be at least partly immerged in an electrolyte in the form of water, in which the marine construction is at least partly immerged, the at least one metal element comprising a metal part, the sacrificial anode being provided for corrosion protection of the metal part. This corrosion protection involves an electrical protection current through an electrical circuit comprising the sacrificial anode, the metal part and the electrolyte.

BACKGROUND OF THE INVENTION

In marine constructions, such as marine vessels and marine structures, a known way to protect an immersed metal part against galvanic corrosion is to provide a sacrificial anode, made of very pure zinc, magnesium, cast iron or an alloy of aluminum, which is directly fastened to, or electrically connected via a cable to the immersed metal part. Thereby, a circuit is provided by an electrical current through the water, serving as an electrolyte, and a surface polarization at the interface between the metal part and the water is created, serving to protect the metal part against corrosion. In such a system with a sacrificial anode, herein referred to as a passive corrosion protection system, or simply a passive system, the sacrificial anode will waste away, preventing damage to the immersed metal part. In some marine corrosion protection systems a passive system is combined with an impressed current cathodic protection (ICCP) system, such as described in U.S. Pat. No. 7,044,075B2.

A problem with passive systems is that the sacrificial anode might be passivated by its surface being covered by a non-conductive oxide layer, (passivation layer), which limits the possible galvanic protection current, so that galvanic corrosion may occur on the metal part which is to be protected. The risk of passivation is specially large if the current drawn from the anode is low for a long period of time, and/or if the salinity of the water is low, such as in the case of marine vessels in brackish or fresh waters.

For marine vessels, a known solution to the stated problem is to lift the boat and remove the passivation layer from the sacrificial anode manually. However, this practice consumes a considerable amount of time and cost. It is also known to use, for sacrificial anodes for boats in fresh water, magnesium which is more reactive than zink or aluminum, and therefore more resistant to passivation. However, magnesium can not be used in salt water, due to over-activity and a very short lifetime.

SUMMARY OF THE INVENTION

It is desirable to improve the corrosion protection by corrosion protection systems in marine constructions.

It is further desirable to prevent passivation of anodes in corrosion protection systems in marine constructions.

It is also desirable to reduce maintenance of corrosion protection systems in marine vessels.

A method according to an aspect of the of the present invention includes connecting at least one of the at least one metal element and the sacrificial anode to a DC electrical power outlet so as to allow an electrical de-passivation current through an electrical circuit comprising the sacrificial anode, the metal element and the electrolyte.

DC electrical power outlet will supply electrical power to the metal element and the sacrificial anode so as to allow the electrical de-passivation current. This will result in gas to be produced underneath at least a part of the passivation layer, so as for the gas to at least partly remove the passivation layer. This will effectively prevent passivation of the sacrificial anode, reducing the risk of a degraded function of the sacrificial anode, thereby improving the corrosion protection by corrosion protection systems in marine constructions. The electrical power can easily be supplied with onboard equipment of a marine vessel while in the water, and reduce the need for lifting the vessel to remove the passivation layer, which in turn reduces maintenance of corrosion protection system. Also, since equipment for supply of electrical power is available on many marine vessels, the invention can be implemented with a minor simple adaptation of existing equipment. In many cases, a simple arrangement including means, for example in the form of a switch, for disconnecting electrically the sacrificial anode from the corrosion protected metal part and connecting the sacrificial anode to a source for the electrical power supply.

It should also be noted that the metal element forming a part of the electrical circuit for the de-passivation current can be any immerged metal element of the marine construction. For example, it can be identical with the metal part that is to be protected from corrosion. Alternatively, it can be a separate metal element, adapted to be lowered by an operator into the water for the de-passivation process, and to be lifted out of the water when said process is completed. However, in a preferred embodiment, the metal element, connected along with the sacrificial anode to the DC electrical power outlet, is a further anode for corrosion protection in the marine construction. In yet more preferred embodiments, the further anode is an active anode of an ICCP system. Thereby, the active anode of the ICCP system can be selectively engaged for the two purposes of providing corrosion protection to the metal part, or some other metal part of the marine construction, and of depassivating the sacrificial anode.

As mentioned further below, depending on the orientation in the circuit of the poles of the DC electrical power outlet, the gas produced to remove the passivation layer can be mainly hydrogen or mainly chlorine gas.

Preferably, the sacrificial anode is connected to a negative pole of the DC electrical power outlet, and the metal element is connected to a positive pole thereof, the metal element comprising a material with a corrosion rate that is substantially lower than the corrosion rate of the sacrificial anode. This is advantageous where the sacrificial anode is connected to the negative pole of the DC electrical power outlet, whereby the sacrificial anode will form a cathode in the circuit for the de-passivation current and the gas produced to remove the passivation layer will be mainly hydrogen. It should be noted that the corrosion rate referred to here is the corrosion rate obtained where an electrical current is applied to the metal element and the sacrificial anode. The corrosion rate of the metal element being substantially lower than the corrosion rate of the sacrificial anode suggests that it is not more than 10% of that rate, preferably less than 0.1%.

Preferably, the step of connecting at least one of the at least one metal element and the sacrificial anode to a DC electrical power outlet is performed repetitively at predetermined time intervals. This will make it possible to provide a simple system at relatively low cost.

In further embodiments, the method comprises measuring an electrical potential of the sacrificial anode with a reference electrode as a ground reference, and determining, based at least partly on said measured electrical potential, whether to perform the step of connecting at least one of the at least one metal element and the sacrificial anode to a DC electrical power outlet. The electrical potential of the sacrificial anode with the reference electrode as a ground reference is indicative of the presence of a passivation layer on the sacrificial anode, and thus it can be used to determine the need for the electric power supply to the sacrificial anode. The determination whether to perform the step of allowing the supply of electrical power to the sacrificial anode and the further anode can comprise comparing the measured electrical potential to a predetermined electrical potential value.

It should be noted that the level of the electrical de-passivation current through the sacrificial anode and the metal element should be sufficient to thoroughly remove any passivisation layer; in principle, the higher the de-passivation current level, the better. In addition, for a sacrificial anode with a large exposed surface, the current should be larger than for an anode with a smaller surface. Also, the duration of the de-passivation current should be sufficient for thorough removal of said layer.

BRIEF DESCRIPTION OF THE DRAWINGS

Below, the invention will be described in detail with reference to the drawings, in which.

DETAILED DESCRIPTION

Figure 1:
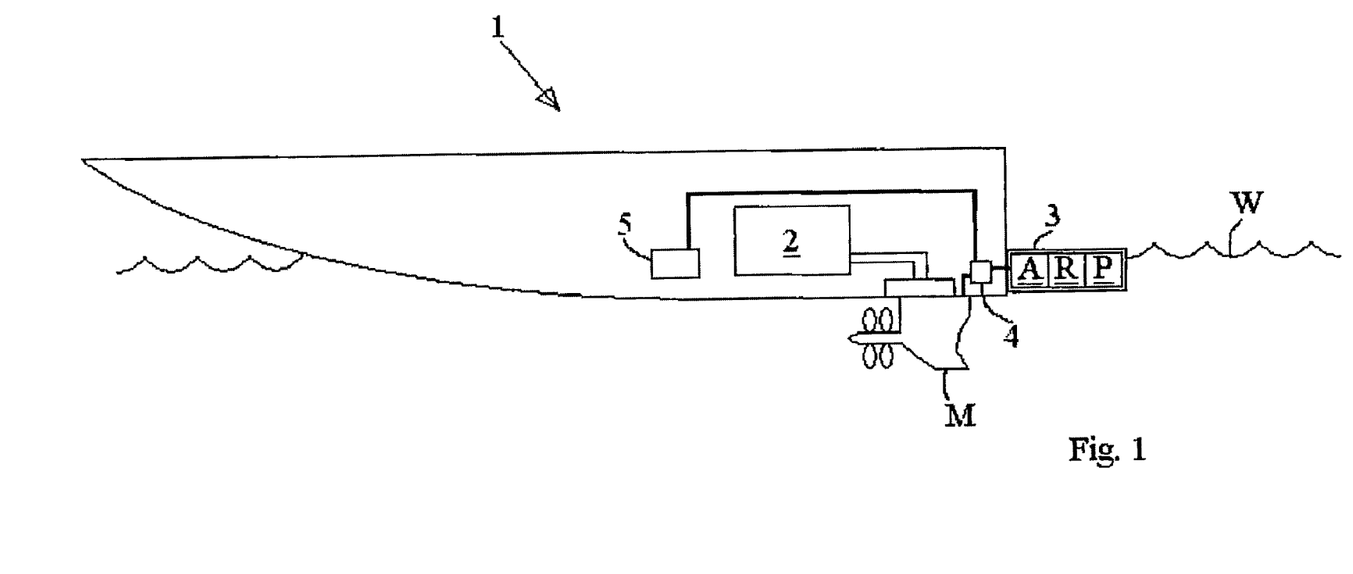
FIG. 1 shows a schematic cross-sectional side view of a boat.

FIG. 1 shows a schematic cross-sectional side view of a marine construction in the form of a boat 1 with a corrosion protection system. The boat 1 is provided with an engine 2 connected to a drive M, with propellers for the propulsion of the boat. In this example, the drive M, immersed in the water W, i.e. sea water, constitutes a metal part to be protected by the corrosion protection system. In FIG. 1, the drive M is schematically presented as a drive manufactured and marketed by Volvo Penta as an IPS (Inboard Performance System) drive, but the invention is of course applicable to boats with any kind of drive, for example a stern drive or a traditional propeller and rudder combination. Also, the invention is applicable to boats with any number of engines and drives.

The corrosion protection system comprises an external unit 3, mounted on a transom of the boat 1. The external unit 3 is adapted to be immersed in the water, and comprises a sacrificial anode P, a further anode in the form of an active anode A, and a reference electrode R. (For a fail-safe function, the external unit 3 can comprise three reference electrodes R, but here only one is discussed for the simplicity of the presentation.) For this presentation, any immersed metal object of the marine construction in addition to the sacrificial anode, such as the drive M, the active anode A or the reference electrode R, is also referred to as a metal element M, A, R.

The active anode A can be provided as one or more platinum coated titanium rods, or MMO (mixed metal oxide) coated titanium rods. Alternative shapes for the active anode A include tubular shapes and shapes as continuous ribbons, and alternative materials include high silicon cast iron, graphite and niobium. The sacrificial anode P can be made in very pure zink. An example of an alternative material for the sacrificial anode P is aluminum. The reference electrode(s) can be supplied in the form of a solid rod made of silver coated with silver chloride, or a solid rod with an electrically conductive core, for example in copper with a silver layer coated with silver chloride.

The corrosion protection system also comprises an electronic control unit (ECU) 4, to which the drive M, the active anode A, and the sacrificial anode P are connected. Also, an electrical power source 5, in the form of a 12 volt DC battery, is connected to the ECU 4. Of course, the DC battery can be adapted to provide any voltage, for example 24 volts.

Figure 2:
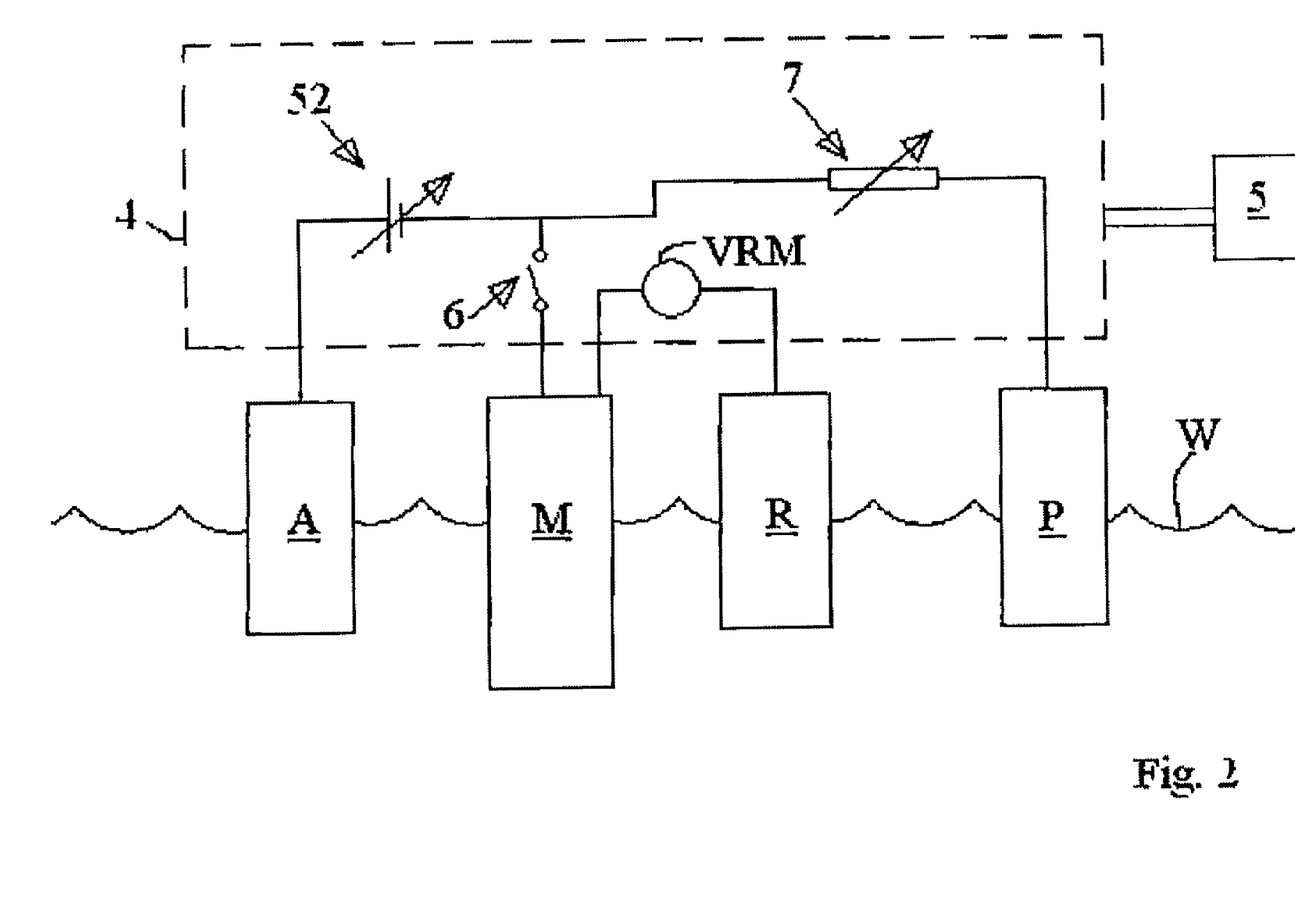
FIG. 2 shows, with parts represented as blocks, a depiction of a corrosion protection system of the boat in FIG. 1.

FIG. 2 shows a schematic representation of the corrosion protection system of the boat in FIG. 1. A switch, herein referred to as a mode switch 6, is controllable by the ECU 4 for selective engagement of one out of two operational modes.

In a corrosion protection mode, the mode switch 6 is set so that the battery 5 via a electrical power outlet 52 is connected to, and adapted to provide DC electrical power to the active anode A and the drive M. The ECU 4 is adapted to measure an electrical potential VRM of the drive M with the reference electrode R as a ground reference. The ECU 4 is further adapted to control, partly based on the measured electrical potential VRM of the drive M, the electrical power supply to the active anode A and the drive M, to thereby control an electrical protection current through an electrical circuit comprising the active anode A, the metal part M and the electrolyte W. The ECU 4 is also adapted to simultaneously control an adjustable resistance 7, in order to control an electrical current IPM through an electrical circuit comprising the passive anode P, the metal part M and the electrolyte W.

As mentioned above, the sacrificial anode P might be passivated by its surface being covered by a non-conductive oxide layer, herein also referred to as a passivation layer. Thus, the ECU 4 is adapted to effect, at predetermined time intervals, a passivation prevention mode, by means of control of the mode switch 6 so as to disconnect the sacrificial anode P from the drive M, whereby the sacrificial anode P will be connected to the battery 5 via the DC electrical power outlet 52.

This will allow supply of electrical power to the sacrificial anode P and the active anode A so as to provide an electrical de-passivation current through an electrical circuit comprising the sacrificial anode P, the active anode A, and the electrolyte W. As indicated in FIG. 2, the positive pole of the DC electrical power outlet 52 is connected to the active anode A, and the negative pole is connected to the sacrificial anode P. As a result, the sacrificial anode P will act as a cathode, and, providing that a sufficient amount of power is supplied, gas in the form of hydrogen will form on the surface of the sacrificial anode P. The hydrogen will be formed underneath any passivation layer formed on the sacrificial anode P, and it will therefore destroy the passivation layer.

In alternative embodiments, a further switch can be controllable by the ECU 4 for selective connection of the reference electrode R to either the drive M or the sacrificial anode P. The ECU 4 can be adapted to control, during the corrosion protection mode, at predetermined time intervals, such a switch so that the reference electrode is disconnected from the drive M and instead connected to the sacrificial anode P. Thereby, the ECU 4 can determine a measured electrical potential of the sacrificial anode P with the reference electrode R as a ground reference. The ECU 4 can further be adapted to compare the measured electrical potential to a predetermined electrical potential value, at which the ECU 4 is adapted to determine based on the comparison whether to effect the passivation prevention mode.

Figure 3:
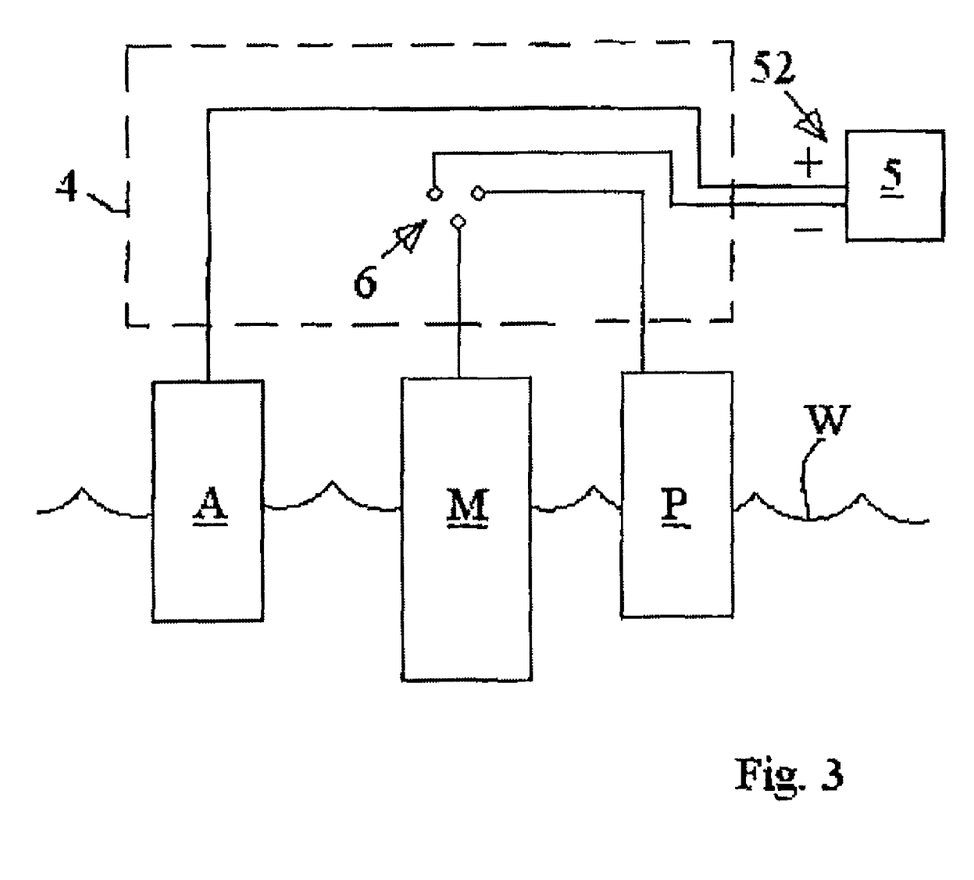
FIG. 3 shows, with parts represented as blocks, a depiction of a corrosion protection system according to an alternative embodiment.

FIG. 3 shows a schematic representation of a corrosion protection system for a drive M according to a further alternative embodiment of the invention. The system comprises a sacrificial anode P, and a metal element, herein referred to as a de-passivation anode A. The de-passivation anode A can for example be made of the any of the materials suggested for the active anode A in the embodiment described above with reference to FIGS. 1 and 2. The corrosion protection system also comprises an ECU 4, to which the drive M, the de-passivation anode A, and the sacrificial anode P are connected. Also, an electrical power source 5, in the form of a 12 volt DC battery, with a DC electrical power outlet 52, is connected to the ECU 4.

Thereby, the positive pole of the battery 5 is connected to the de-passivation anode A.

A mode switch 6 is controllable by the ECU 4 for selective engagement of one out of two operational modes. By means of the mode switch 6, a corrosion protection mode can be effected by connecting the drive M to the sacrificial anode P, for corrosion protection of the drive M. The ECU 4 is adapted to control, at predetermined time intervals, the mode switch 6 so that the sacrificial anode P is disconnected from the drive M and instead connected to the negative pole of the battery 5, in order to effect a passivation prevention mode. This will allow supply of electrical power to the sacrificial anode P and the de-passivation anode A so as to provide an electrical de-passivation current through an electrical circuit comprising the sacrificial anode P, the de-passivation anode A, and the electrolyte W.

As a result of the positive pole of the battery 5 being connected to the de-passivation anode A, and the negative pole being connected to the sacrificial anode P, the sacrificial anode P will act as a cathode, and gas in the form of hydrogen will form on the surface of the sacrificial anode P, destroying any passivation layer. By control of the mode switch 6, the ECU 4 is adapted to terminate the passivation prevention mode after a predetermined time interval from its initiation.

As an alternative, the negative pole of the battery 5 could be connected to the de-passivation anode A, and the positive pole could be connected to the sacrificial anode P, whereby the de-passivation anode A will act as a cathode, and gas in the form of chlorine gas will form on the surface of the sacrificial anode P, destroying any passivation layer on it.

Figure 4:
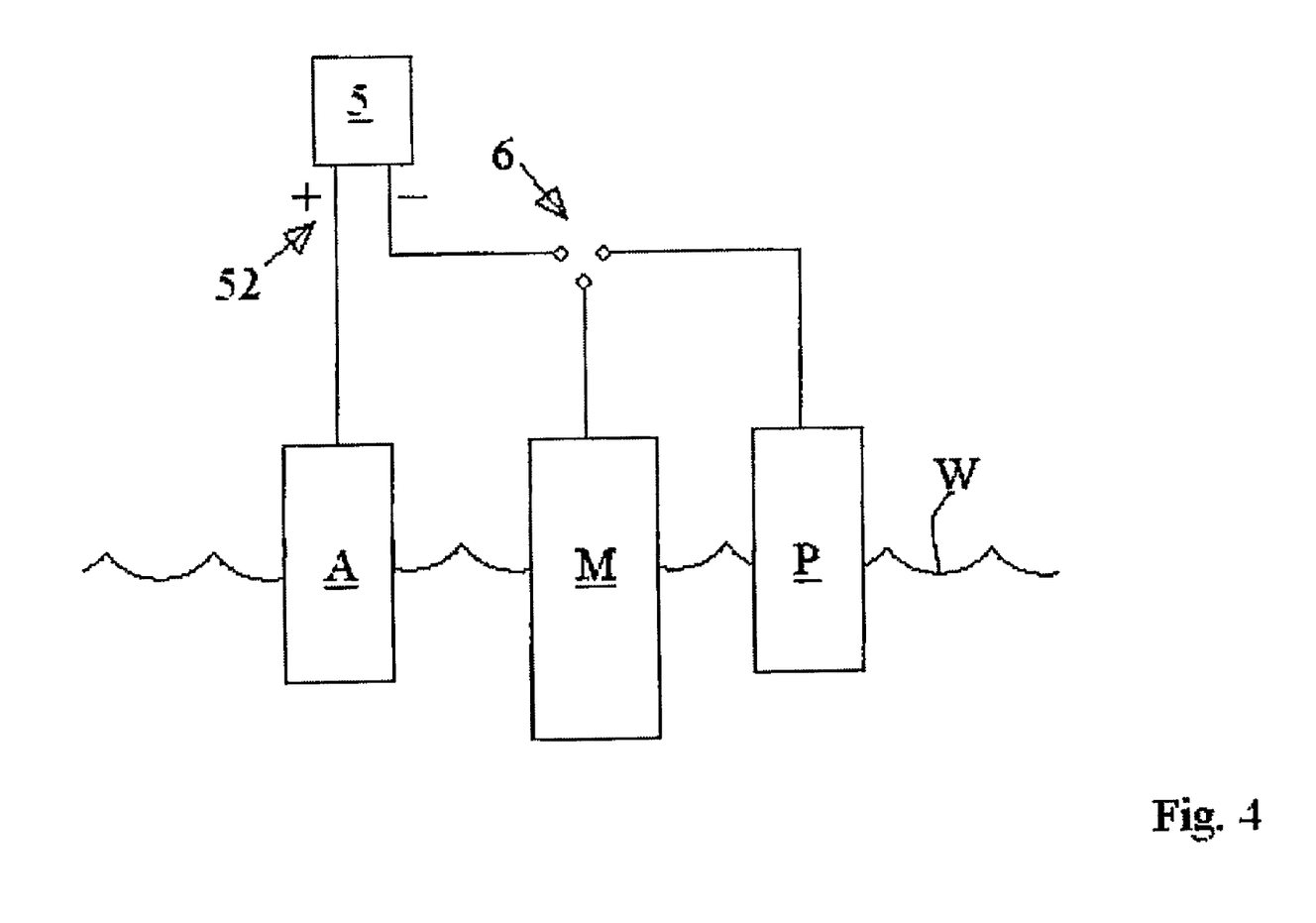
FIG. 4 shows, with parts represented as blocks, a depiction of a corrosion protection system according to a further alternative embodiment of the invention.

FIG. 4 shows a schematic representation of a corrosion protection system for a drive M in another embodiment of the invention. As in the embodiment described with reference to FIG. 3, the system comprises a sacrificial anode P, and a metal element in the form of a de-passivation anode A. The positive pole of a 12 volt DC battery 5, with a DC electrical power outlet 52, is connected to the de-passivation anode A.

The negative pole of the battery 5 is connected to a mode switch 6 which is manually controllable by an operator for selective engagement of one out of two operational modes. More specifically, by means of the mode switch 6, a corrosion protection mode can be effected by connecting the drive M to the sacrificial anode P, for corrosion protection of the drive M. The operator can, for example at prescribed routine intervals, maneuver the mode switch 6 so that the sacrificial anode P is disconnected from the drive M and instead connected to the negative pole of the battery 5, in order to effect a passivation prevention mode. As mentioned above, this will result in gas in the form of hydrogen being formed on the surface of the sacrificial anode P, destroying any passivation layer. By control of the mode switch 6, the operator can terminate the passivation prevention mode after a prescribed time interval from its initiation.

Figure 5:
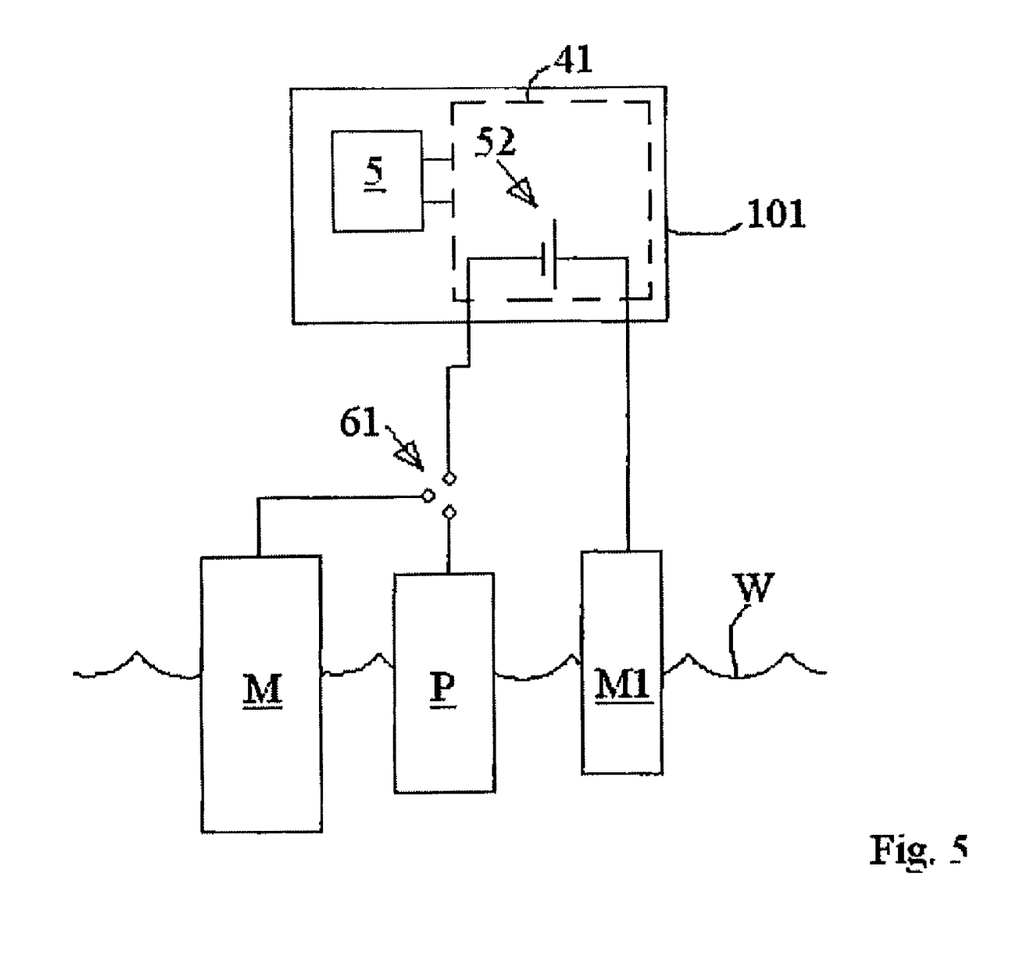
FIG. 5 depicts a corrosion protection system with an auxiliary unit device.

FIG. 5 depicts a corrosion protection system in yet another embodiment of the invention. A boat (not shown) comprises a drive M protected by a sacrificial anode P. A separate auxiliary device 101, which is adapted to be transported by a person, comprises a battery 5, and is connected to a separate metal element M1, adapted to be lowered by a person into the water for a de-passivation process of the sacrificial anode P, and to be lifted out of the water when said process is completed.

On the boat a terminal 61 is provided to disconnect the sacrificial anode P from the drive M, and to connect the sacrificial anode P to the auxiliary device 101. Thereby, the auxiliary device 101 provides a connection of the sacrificial anode P and the separate metal element M1 to a DC electrical power source 52 in the auxiliary device 101, in turn fed from the battery 5. This connection allows an electrical de-passivation current through an electrical circuit comprising the sacrificial anode P, the separate metal element M1 and the water W.

The auxiliary device 101 comprises an ECU 41, adapted to discontinue the de-passivation current after a predetermined time interval. Alternatively, the auxiliary device 101 can be adapted for the de-passivation process to be terminated by an operator, at which the ECU 41 can be omitted.

As an alternative, the metal element used for the de-passivation of the sacrificial anode P could be, instead of a separate metal element M1, the drive M. It should also be noted that in alternative embodiments, the auxiliary device could be adapted to the connected to a battery provided in the boat.

The invention claimed is:

1. A method for corrosion protection in a marine construction, such as a marine surface vessel or a marine structure, the marine construction comprising at least one metal element and a sacrificial anode adapted to be at least partly immersed in an electrolyte in the form of water, in which the marine construction is at least partly immersed, the at least one metal element comprising a metal part, the sacrificial anode being provided for corrosion protection of the metal part, comprising connecting at least one of the at least one metal element and the sacrificial anode to a DC electrical power outlet so as to allow an electrical de-passivation current through an electrical circuit comprising the sacrificial anode, the metal element and the electrolyte, the method further comprising measuring an electrical potential of the sacrificial anode with a reference electrode (R) as a ground reference, and determining, based at least partly on the measured electrical potential, whether to perform the step of connecting at least one of the at least one metal element and the sacrificial anode to a DC electrical power outlet.

2. A method according to claim 1 wherein the metal element, connected along with the sacrificial anode to the DC electrical power outlet, is a further anode for corrosion protection in the marine construction.

3. A method according to claim 2, wherein the further anode is an active anode of an impressed current cathodic protection system.

4. A method according to claim 1 wherein the sacrificial anode is connected to a negative pole of the DC electrical power outlet, and the metal element is connected to a positive pole thereof, the metal element comprising a material with a corrosion rate that is substantially lower than the corrosion rate of the sacrificial anode.

5. A method according to claim 1, comprising performing the step of connecting at least one of the at least one metal element and the sacrificial anode to a DC electrical power outlet repetitively at predetermined time intervals.

6. A marine surface vessel comprising at least one metal element and a sacrificial anode adapted to be at least partly immersed in an electrolyte in the form of water, in which the marine surface vessel is at least partly immersed, the at least one metal element comprising a metal part, the sacrificial anode being provided for corrosion protection of the metal part, wherein wherein at least one of the at least one metal element (M. A, R, M1) and the sacrificial anode are arranged to be connected to a DC electrical power outlet so as to allow an electrical de-passivation current through an electrical circuit comprising the sacrificial anode, the metal element and the electrolyte, wherein the marine surface vessel is adapted to measure an electrical potential of the sacrificial anode with a reference electrode as a ground reference, and to determine, based at least partly on the measured electrical potential, whether to connect the at least one of the at least one metal element and the sacrificial anode to the DC electrical power outlet.

7. A marine surface vessel according to claim 6, wherein the metal element, arranged to be connected along with the sacrificial anode to the DC electrical power outlet, is a further anode (A) for corrosion protection in the marine construction.

8. A marine surface vessel according to claim 7, wherein the further anode is an active anode of an impressed current cathodic protection system.

9. A marine surface vessel according to claim 6, comprising means for disconnecting electrically the sacrificial anode from the metal part and connecting the sacrificial anode to the DC electrical power outlet.

10. A marine surface vessel according to claim 6, wherein the sacrificial anode is arranged to be connected to a negative pole of the DC electrical power outlet, and the metal element is arranged to be connected to a positive pole thereof, the metal element comprising a material with a corrosion rate that is substantially lower than the corrosion rate of the sacrificial anode.

11. A marine surface vessel according to claim 6, wherein the metal element and the sacrificial anode are arranged to be connected to the DC electrical power outlet repetitively at predetermined time intervals.

12. A marine surface vessel according to claim 6, comprising an electronic control unit adapted to connect the at least one of the at least one metal element and the sacrificial anode to the DC electrical power outlet.

13. An auxiliary device adapted to provide a connection from a DC electrical power outlet to at least one of at least one metal element and to a reference electrode, and to a sacrificial anode of a marine construction, comprising the at least one metal element, the reference electrode, and the sacrificial anode being at least partly immersed in an electrolyte (W) in the form of water, in which the marine construction is at least partially immersed, the at least one metal element comprising a metal part, the sacrificial anode being provided for corrosion protection of the metal part, the connection of the DC electrical power outlet to the at least one of the at least one metal element, to a reference electrode, and to the sacrificial anode allowing an electrical de-passivation current through an electrical circuit comprising the at least one of the at least one metal element, the sacrificial anode and the electrolyte.

* * * * *